US011938501B2

United States Patent
Nezu

(10) Patent No.: US 11,938,501 B2
(45) Date of Patent: Mar. 26, 2024

(54) NOZZLE DEVICE

(71) Applicant: NIFCO INC., Yokosuka (JP)

(72) Inventor: Mikio Nezu, Yokosuka (JP)

(73) Assignee: NIFCO INC., Yokosuka (JP)

( * ) Notice: Subject to any disclaimer, the term of this patent is extended or adjusted under 35 U.S.C. 154(b) by 457 days.

(21) Appl. No.: 17/259,255

(22) PCT Filed: Jul. 5, 2019

(86) PCT No.: PCT/JP2019/026845
§ 371 (c)(1),
(2) Date: Jan. 11, 2021

(87) PCT Pub. No.: WO2020/017363
PCT Pub. Date: Jan. 23, 2020

(65) Prior Publication Data
US 2021/0268532 A1 Sep. 2, 2021

(30) Foreign Application Priority Data
Jul. 20, 2018 (JP) ................................. 2018-136932

(51) Int. Cl.
*B05B 15/74* (2018.01)
*A61L 9/14* (2006.01)
(Continued)

(52) U.S. Cl.
CPC ............... *B05B 15/74* (2018.02); *A61L 9/14* (2013.01); *B05B 1/306* (2013.01); *B60H 3/0007* (2013.01); *A61L 2209/134* (2013.01)

(58) Field of Classification Search
CPC ......... B05B 15/74; B05B 1/306; B05B 1/005; B05B 1/323; B05B 1/30; A61L 9/14; A61L 2209/134; B60H 3/0007
See application file for complete search history.

(56) References Cited

U.S. PATENT DOCUMENTS

| 8,905,327 | B2 | 12/2014 | Hartnell |
| 2007/0095935 | A1* | 5/2007 | Katzman ................. B05B 3/063 239/204 |
| 2015/0138357 | A1 | 5/2015 | Romack et al. |

FOREIGN PATENT DOCUMENTS

| DE | 101 25 898 A1 | 12/2001 |
| EP | 2 371 636 A1 | 10/2011 |

(Continued)

OTHER PUBLICATIONS

International Search Report for PCT/JP2019/026845 dated Sep. 17, 2019 (PCT/ISA/210).

(Continued)

*Primary Examiner* — Qingzhang Zhou
(74) *Attorney, Agent, or Firm* — Sughrue Mion, PLLC

(57) ABSTRACT

A nozzle device 1 includes a main body 10 that is formed of a main-body first member 11 and a main-body second member 22 and that has an internal accommodation space 21 in which members are accommodated, a movable nozzle portion 30 that is accommodated in the accommodation space 21, and a coil spring 2 that is disposed between the movable nozzle portion 30 and the main body 10. When air is supplied to a main-body flow-path portion 23 from below, the flow path of the air is changed by the Coanda effect in an air guiding portion 27 such that the air flows along the air guiding portion 27, and the air flows into a gap between an air receiving portion 36 and the air guiding portion 27 and is guided to the air receiving portion 36. The air is pressurized in the air receiving portion 36 and pushes up the movable nozzle portion 30.

8 Claims, 5 Drawing Sheets

(51) Int. Cl.
*B05B 1/30* (2006.01)
*B60H 3/00* (2006.01)

(56) References Cited

FOREIGN PATENT DOCUMENTS

| | | | |
|---|---|---|---|
| FR | 2738166 | * | 3/1997 |
| JP | 39-32350 | * | 10/1964 |
| JP | 39-032350 | Y1 | 10/1964 |
| JP | 05-054124 | U | 7/1993 |
| JP | 06-343907 | A | 12/1994 |
| JP | 07-149208 | A | 6/1995 |
| JP | 10-244186 | A | 9/1998 |
| JP | 2017-533006 | A | 11/2017 |
| WO | 2016/050400 | A1 | 4/2016 |

OTHER PUBLICATIONS

Communication dated Mar. 24, 2022, issued in German Application No. 11 2019 003 675.0.

* cited by examiner

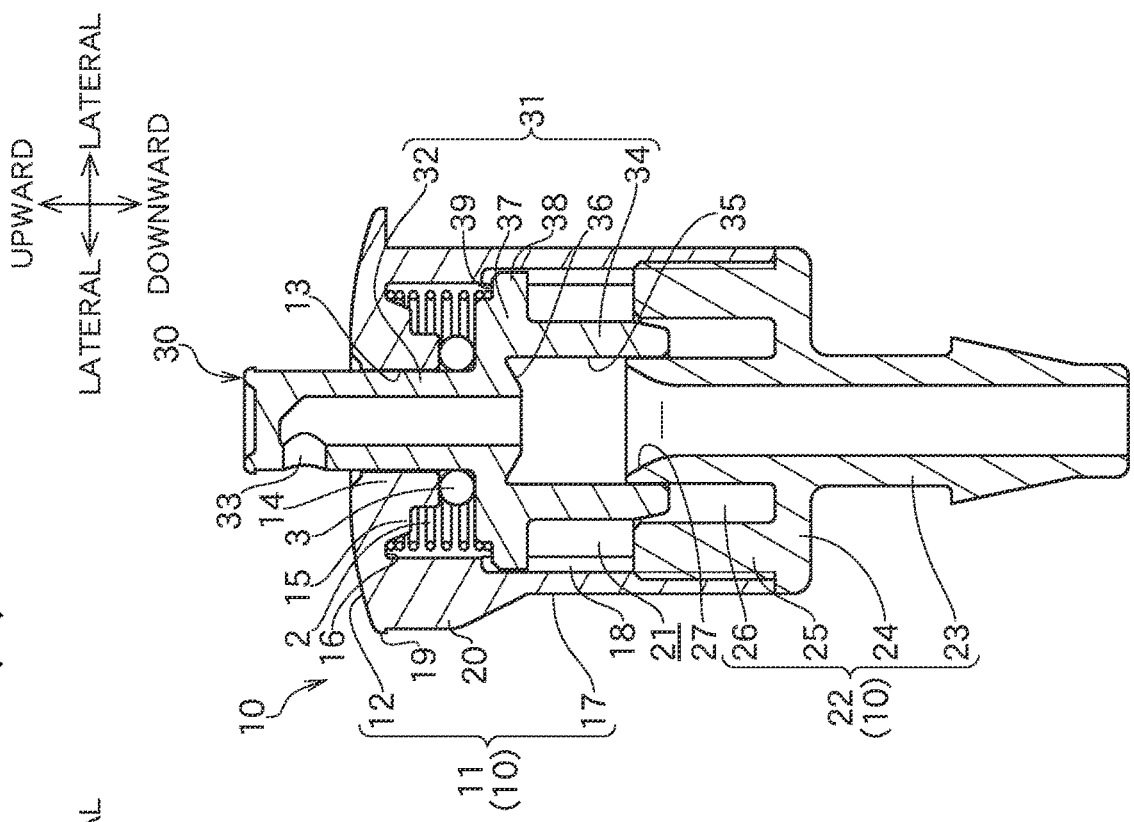
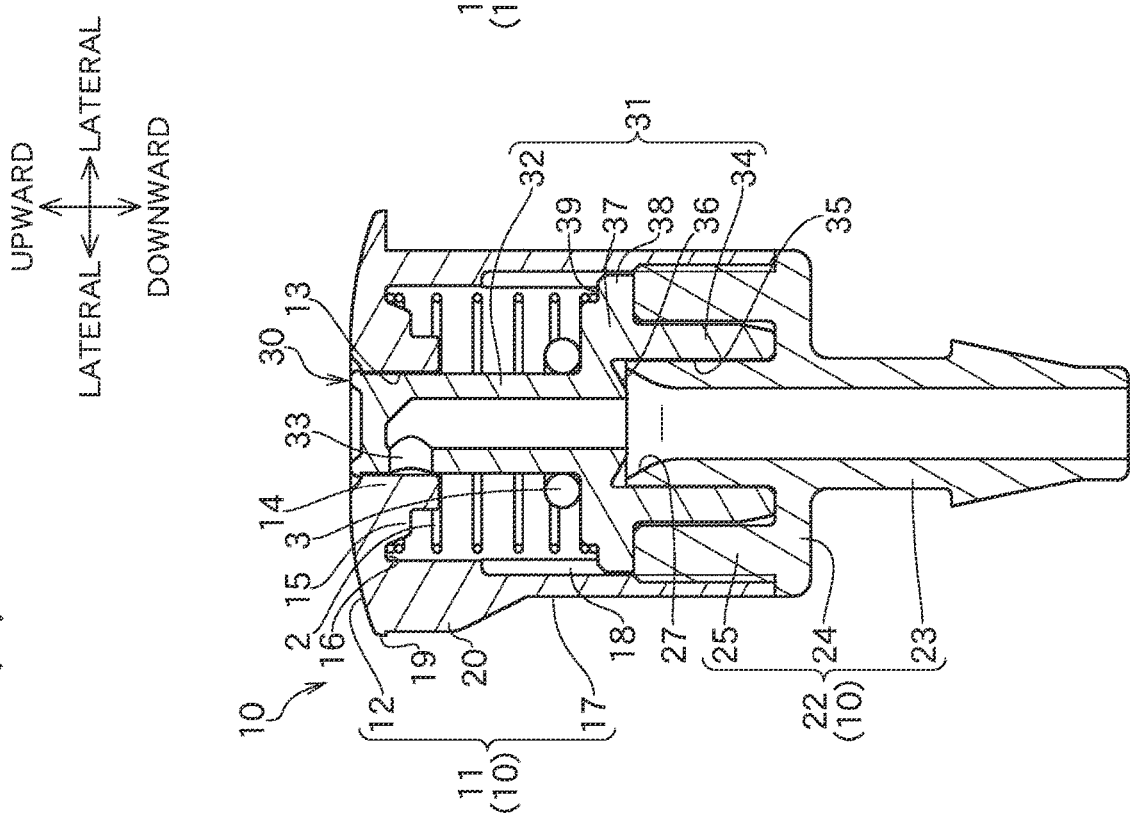

even though the air-use efficiency is not favorable.

NOZZLE DEVICE

CROSS REFERENCE TO RELATED APPLICATIONS

This application is a National Stage of International Application No. PCT/JP2019/026845 filed Jul. 5, 2019, claiming priority based on Japanese Patent Application No. 2018-136932 filed Jul. 20, 2018.

DESCRIPTION

Technical Field

The present invention relates to a nozzle device that ejects a fluid.

Background Art

In the related art, a nozzle device described in PTL 1 is known as an example of a device that ejects a fluid such as a liquid or a gas. In this nozzle device, a nozzle is attached to a piston accommodated in a cylinder, and the nozzle moves back and forth as a result of the piston being operated. In other words, air moves the piston forward in the cylinder so as to expose the nozzle, and the air is ejected from the exposed nozzle. In contrast, when supply of the air is stopped, the piston is retracted by a spring, and the nozzle returns to its original position.

CITATION LIST

Patent Literature

PTL 1: Japanese Unexamined Patent Application Publication No. 6-343907

SUMMARY OF INVENTION

Technical Problem

In the above-described nozzle device, however, the air leaks from the nozzle when the air pushes the piston, so that the pressure pushing the piston is reduced, and accordingly, the air-use efficiency is not favorable. If the capacity of an air pump is increased in order to maintain the pressure that pushes the piston, the size of the air pump increases, and there will be problems such as selection of an installation space, an increase in weight, and an increase in price. Similar problems will occur even if the fluid is a liquid.

The present invention has been made in view of the above situation. In other words, it is an object of the present invention to provide a nozzle device capable of improving fluid-use efficiency independently of the specifications of a pump.

Solution to Problem

To achieve the above-mentioned object, a nozzle device according to the present invention includes a main body that is mounted on a vehicle body and that includes a main-body flow-path portion serving as a flow path of a fluid and a movable nozzle portion that is accommodated in the main body and that is caused, by a fluid, to move from a non-usage position at which an ejection port is accommodated in the main body to a usage position at which the ejection port is exposed outside of the main body. A nozzle flow-path portion that is included in the movable nozzle portion and that communicates with the main-body flow-path portion includes a fluid receiving portion that is formed in such a manner as to extend outward than a downstream side and in such a manner as to be inclined in a direction in which the movable nozzle portion moves to a usage position.

In the nozzle device according to the present invention, the fluid receiving portion is included in the nozzle flow-path portion and formed at a position facing a downstream end portion of the main-body flow-path portion, and a gap is formed between the fluid receiving portion and the downstream end portion.

In the nozzle device according to the present invention, the movable nozzle portion includes a surrounding-wall portion that extends from the fluid receiving portion toward an upstream side and that is located on an outer side of the main-body flow-path portion.

In the nozzle device according to the present invention, a downstream end portion of the main-body flow-path portion includes a fluid guiding portion that extends outward than the upstream side and that is inclined in a direction in which the movable nozzle portion moves to a usage position.

In the nozzle device according to the present invention, the ejection port that is accommodated is blocked by the main body.

In the nozzle device according to the present invention, a fluid has a scent.

In the nozzle device according to the present invention, the main body includes an accommodation space in which the movable nozzle portion is accommodated, the main-body flow-path portion that has a downstream-side portion projecting toward the accommodation space, and an exposed-surface portion that has a hole formed so as to be coaxial with the main-body flow-path portion and that is exposed to a side of a vehicle body on which a fluid is ejected. The movable nozzle portion includes a support-plate portion that is formed on an outer periphery of the nozzle flow-path portion. The ejection port is formed in a side surface of the nozzle flow-path portion. In the accommodation space, a first elastic member and a second elastic member are provided between the exposed-surface portion and the support-plate portion, the first elastic member being configured to move the movable nozzle portion, and the second elastic member being interposed between the exposed-surface portion and the support-plate portion.

In the nozzle device according to the present invention, a fluid is air. Advantageous Effects of Invention The nozzle device according to the present invention includes the main body that is mounted on the vehicle body and that includes the main-body flow-path portion serving as the flow path of the fluid and the movable nozzle portion that is accommodated in the main body and that is caused, by the fluid, to move from the non-usage position at which the ejection port is accommodated in the main body to the usage position at which the ejection port is exposed outside of the main body. The nozzle flow-path portion that is included in the movable nozzle portion and that communicates with the main-body flow-path portion includes the fluid receiving portion that is formed in such a manner as to extend outward than the downstream side and in such a manner as to be inclined in the direction in which the movable nozzle portion moves to the usage position. In other words, the fluid receiving portion is recessed in the direction in which the movable nozzle portion moves to the usage position, and thus, the fluid flows into the fluid receiving portion. The movable nozzle portion is pushed by the fluid pressure in the fluid receiving portion and moves to the usage position.

Therefore, the fluid-use efficiency can be improved. This is independent of the specifications of a pump and thus does not affect the size, the weight, and the price of the pump.

In the nozzle device according to the present invention, the fluid receiving portion is included in the nozzle flow-path portion and formed at the position facing the downstream end portion of the main-body flow-path portion, and a gap is formed between the fluid receiving portion and the downstream end portion. In other words, the fluid receiving portion is formed in the movable nozzle portion so as to be positioned near the main body and so as to be located on a relatively upstream side. With this configuration, the fluid flows into the fluid receiving portion, and the movable nozzle portion is pushed by the fluid pressure from a relatively upstream side. Thus, the movable nozzle portion can be easily moved. In addition, since the fluid is pressurized as a result of flowing into the gap, the movable nozzle portion can be easily moved by the increased pressure.

In the nozzle device according to the present invention, the movable nozzle portion includes the surrounding-wall portion that extends from the fluid receiving portion toward an upstream side and that is located on an outer side of the main-body flow-path portion. In other words, the outer periphery of the main-body flow-path portion is covered with the surrounding-wall portion, so that leakage of the fluid from a downstream end portion of the main-body flow-path portion can be suppressed.

In the nozzle device according to the present invention, the downstream end portion of the main-body flow-path portion includes the fluid guiding portion that extends outward than the upstream side and that is inclined in a direction in which the movable nozzle portion moves to a usage position. In other words, the flow path of the fluid is changed by the Coanda effect, and the fluid flows along the fluid guiding portion and is guided to the fluid receiving portion. Therefore, the movable nozzle portion can be suitably pushed by increasing the pressure in the fluid receiving portion.

In the nozzle device according to the present invention, the ejection port that is accommodated is blocked by the main body. With this configuration, the fluid is supplied while the ejection port is blocked, and thus, the fluid does not leak from the ejection port and is pressurized in the flow path. Therefore, the fluid-use efficiency can be improved.

In the nozzle device according to the present invention, the fluid has the scent. In other words, the scented fluid is ejected in a vehicle, so that various stimuli can be given to the driver and the fellow passenger in accordance with the type of scent.

In the nozzle device according to the present invention, the main body includes the accommodation space in which the movable nozzle portion is accommodated, the main-body flow-path portion that has the downstream-side portion projecting toward the accommodation space, and the exposed-surface portion that has the hole formed so as to be coaxial with the main-body flow-path portion and that is exposed to a side of the vehicle body on which the fluid is ejected. The movable nozzle portion includes the support-plate portion that is formed on the outer periphery of the nozzle flow-path portion. The ejection port is formed in the side surface of the nozzle flow-path portion. In the accommodation space, the first elastic member and a second elastic member are provided between the exposed-surface portion and the support-plate portion, the first elastic member being configured to move the movable nozzle portion, and the second elastic member being interposed between the exposed-surface portion and the support-plate portion. With this configuration, when the fluid flows into the fluid receiving portion through the main-body flow-path portion, the fluid is pressurized in the flow path without leaking from the ejection port, and the movable nozzle portion is pushed by the fluid pressure and moves to the usage position. In this case, the second elastic member is sandwiched between the exposed-surface portion and the support-plate portion, so that generation of noise by contact between the exposed-surface portion and the support-plate portion can be suppressed, and a gap between the main body and the movable nozzle portion can be sealed. In contrast, when supply of the fluid is stopped, the support-plate portion is pushed by the restoring force of the first elastic member, so that the movable nozzle portion can return to the non-usage position.

In the nozzle device according to the present invention, the fluid is air. Thus, the above-described advantageous effects can be obtained in the dry atmosphere.

BRIEF DESCRIPTION OF DRAWINGS

FIGS. 4(a) and 4(b) each illustrate a cross section of the nozzle device according to the first embodiment of the present invention in an enlarged manner. FIG. 4(a) is an enlarged sectional view taken along line II-A of FIG. 2(a) illustrating the state in which the movable nozzle portion is located at the non-usage position, and FIG. 4(b) is an enlarged sectional view taken along line III-A of FIG. 3(a) illustrating the state in which the movable nozzle portion is located at the usage position.

FIG. 5(a) is an enlarged sectional view of a principal portion of a nozzle device according to a second embodiment of the present invention. FIG. 5(b) is an enlarged sectional view of a principal portion of a nozzle device according to a third embodiment of the present invention. FIG. 5(c) is an enlarged sectional view of a principal portion of a nozzle device according to a fourth embodiment of the present invention.

DESCRIPTION OF EMBODIMENTS

Figure 1A:
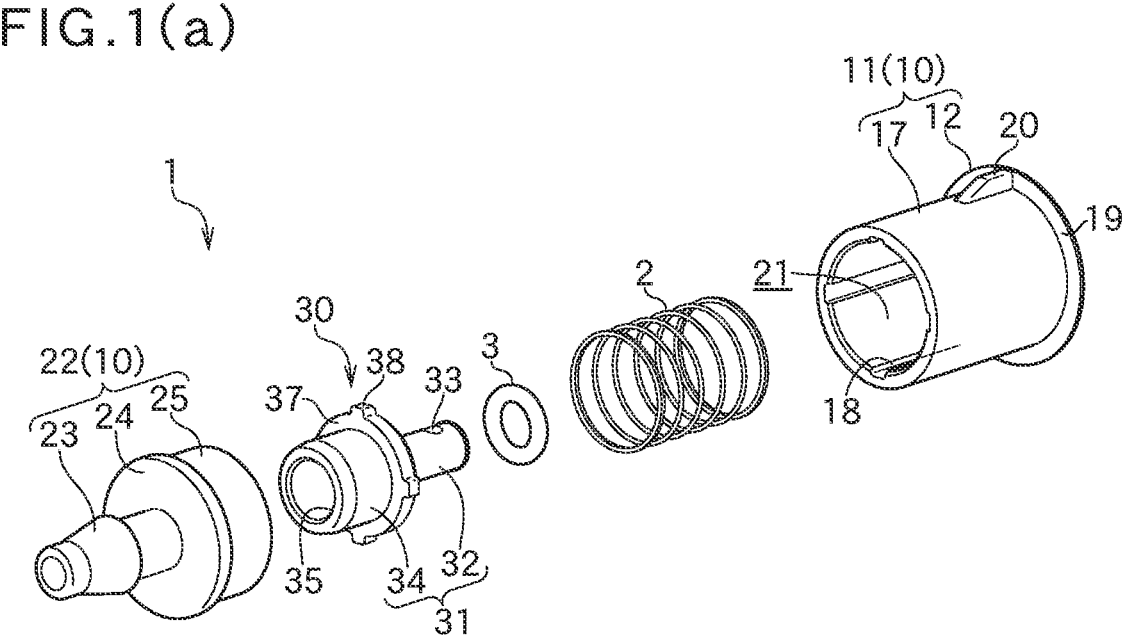
FIGS. 1(a) and 1(b) illustrate a nozzle device according to a first embodiment of the present invention in an exploded manner and are an exploded perspective view and an exploded sectional perspective view, respectively.
Figure 1B:
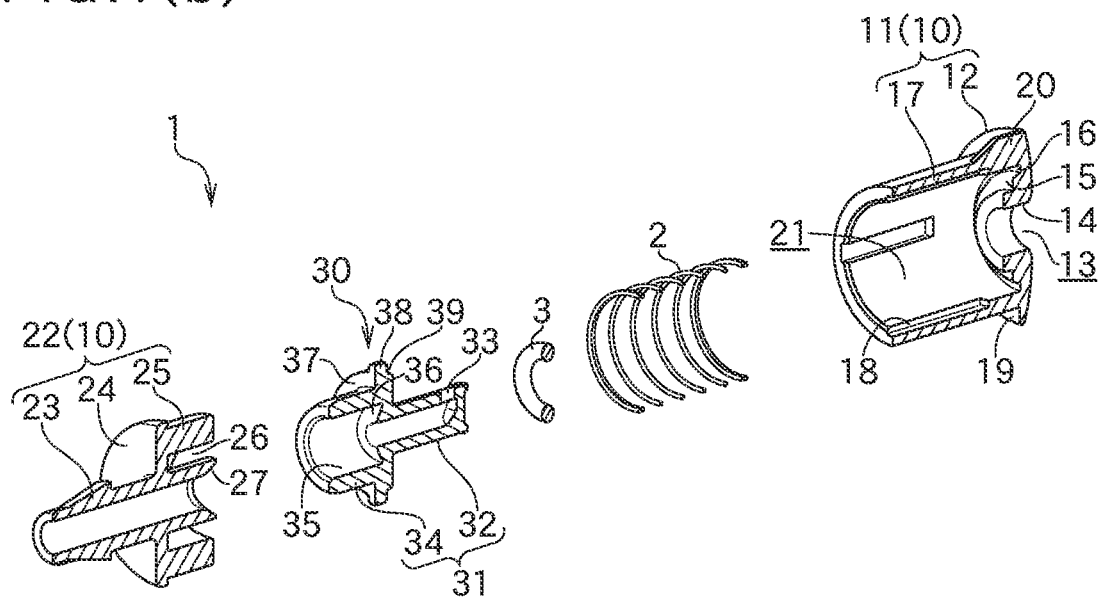

A nozzle device according to the first embodiment of the present invention will be described below with reference to the drawings. FIGS. 1(a) and 1(b) illustrate a nozzle device 1 in an exploded manner. FIGS. 2(a), 2(b), 2(c), and 2(d) and FIGS. 3(a), 3(b), 3(c), and 3(d) each illustrate the nozzle device 1 in an assembled state. FIGS. 4(a) and 4(b) each illustrate a cross section of the nozzle device 1 in an enlarged manner.

As illustrated in FIGS. 1(a) and 1(b), the nozzle device 1 includes a main body 10 that is formed of two members, which are combined together, and that has an internal accommodation space 21 in which members are accommodated, a movable nozzle portion 30 that is accommodated in the accommodation space 21 of the main body 10, a coil spring 2 that serves as a first elastic member and that is disposed between the movable nozzle portion 30 and the main body 10, and an O-ring 3 that serves as a second elastic member. As illustrated in FIGS. 2(a), 2(b), 2(c), and 2(d) and FIGS. 3(a), 3(b), 3(c), and 3(d), the nozzle device 1, which is formed by assembling the members, is mounted onto, for example, a vehicle body of an automobile (not illustrated) such that the main body 10 is partially built into the vehicle body. Here, the "vehicle body" includes not only exterior components such as various lights and cameras but also interior components such as an instrument panel and a console. In other words, air that is ejected from the nozzle device 1 is blown onto each portion of the vehicle body, so that waterdrops or foreign matters on a surface of the corresponding light or camera are blown off, or scented air is jetted out from the instrument panel or the console, so that various stimuli are given to a driver and a fellow passenger. Although air is ejected in the first embodiment, the fluid that is ejected from the nozzle device 1 may be a liquid. In this case, the liquid that is sprayed onto the surfaces of the lights, the cameras, and the like is, for example, water, a chemical solution, a detergent, or the like, and the liquid that is jetted out from the instrument panel or the console is in the form of fine atomized particles. In addition, the nozzle device 1 can select the fluid to be used, and a liquid or the air is selected each time depending on the application.

Figure 2A:
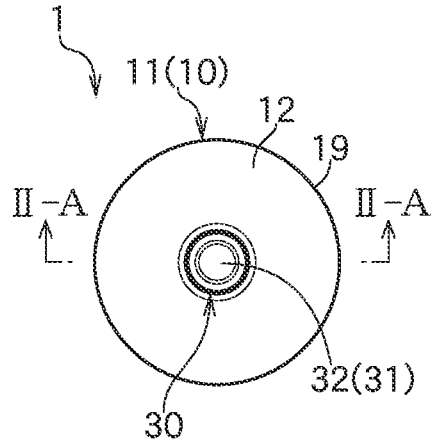
FIGS. 2(a), 2(b), 2(c), and 2(d) illustrate the nozzle device according to the first embodiment of the present invention in a state where a movable nozzle portion is located at a non-usage position and are a plan view, a perspective view, a side view, and a bottom view, respectively.
Figure 2B:
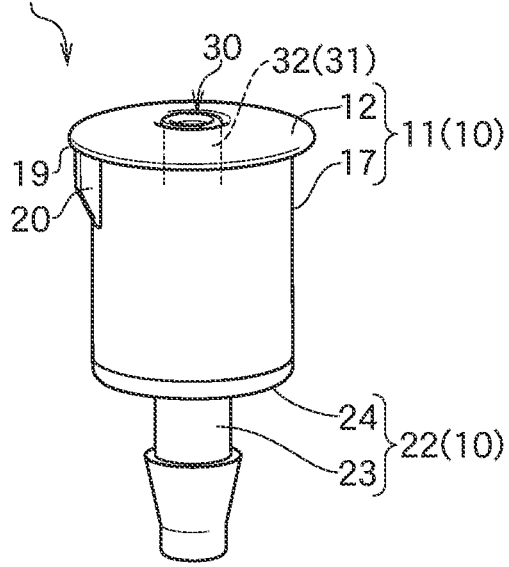
Figure 2C:
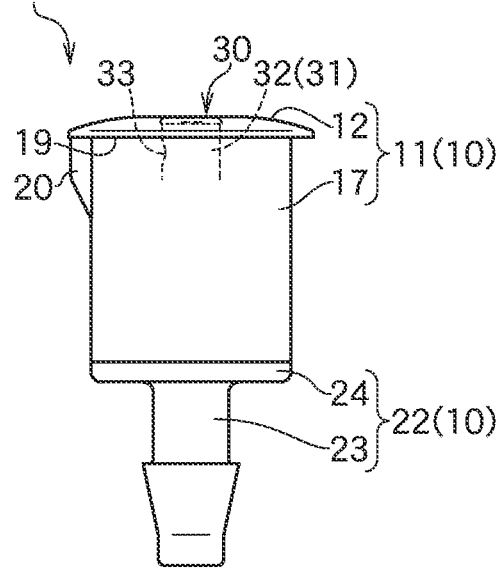
Figure 2D:
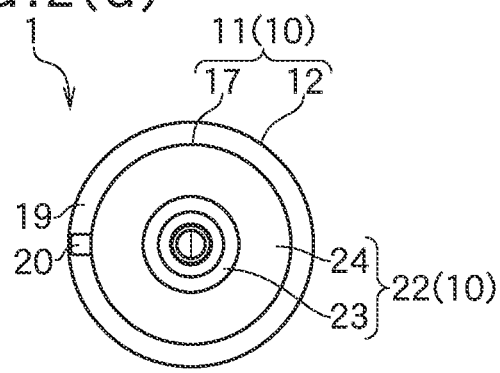
Figure 3A:
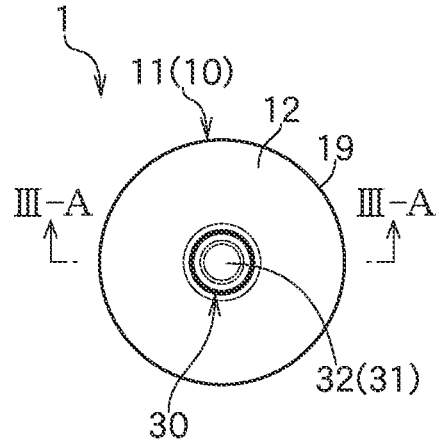
FIGS. 3(a), 3(b), 3(c), and 3(d) illustrate the nozzle device according to the first embodiment of the present invention in a state where the movable nozzle portion is located at a usage position and are a plan view, a perspective view, a side view, and a bottom view, respectively.
Figure 3B:
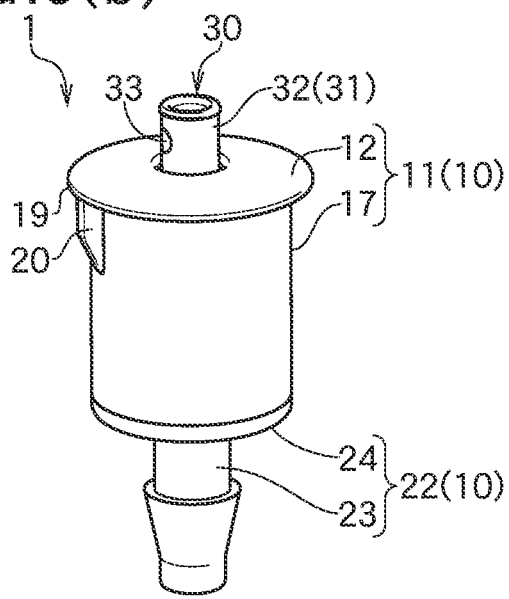
Figure 3C:
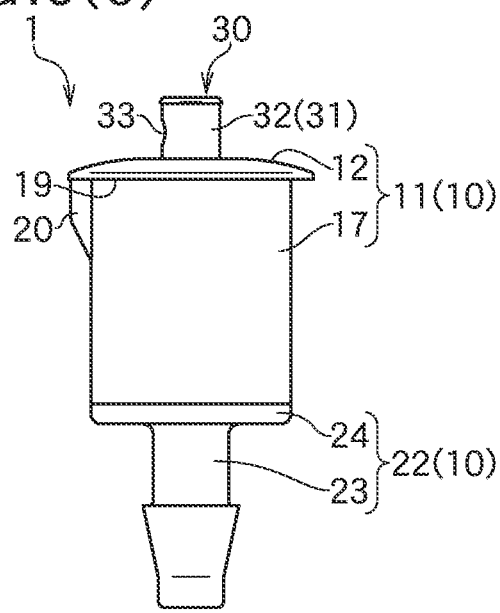
Figure 3D:
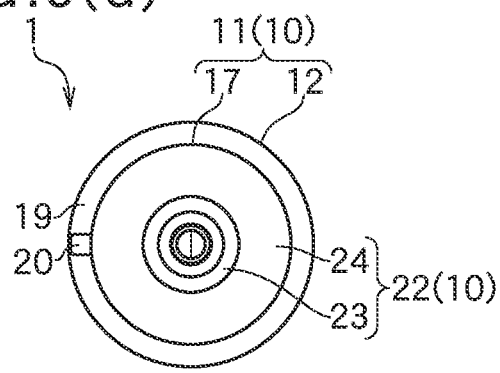

Note that, in the following description, regarding directions in which the movable nozzle portion 1 moves, a direction from a non-usage position at which an ejection port 33 is accommodated in the main body 10 (see FIG. 2(c) and FIG. 4(a)) to a usage position at which the ejection port 33 is exposed outside of the main body 10 (see FIG. 3(c) and FIG. 4(b)) will be referred to as an upward direction, and a direction from the non-usage position toward the usage position will be referred to as a downward direction. A direction perpendicular to the upward and downward directions will be referred to as a lateral direction (see FIGS. 4(a) and 4(b)). The flow path of the air extends from the lower side toward the upper side.

As illustrated in FIGS. 1(a) and 1(b), the main body 10 is formed of a main-body first member 11 and a main-body second member 22. The main-body first member 11 includes an exposed-surface portion 12 that has a circular plate-like shape and that is exposed to the side of a vehicle body on which the air is ejected and a cylindrical outer peripheral portion 17 that is connected to the exposed-surface portion 12 and that is built into the vehicle body. The exposed-surface portion 12 has a hole 13 formed at the center thereof. A ring-shaped sealing projection 14 is formed on a lower surface of the exposed-surface portion 12 in such a manner as to project around the periphery of the hole 13. The outer periphery of the sealing projection 14 has a step portion 15, and a ring-shaped main-body groove 16 is formed in the outer periphery of the step portion 15. A plurality of guide grooves 18 is formed in the inner side of the outer peripheral portion 17. The guide grooves 18 each extend linearly in the vertical direction and are arranged in such a manner as to be equally spaced in the circumferential direction of the outer peripheral portion 17. In a portion in which the exposed-surface portion 12 and the outer peripheral portion 17 are connected to each other, the exposed-surface portion 12 projects laterally from the outer peripheral portion 17 such that a ring-shaped flange 19 is formed. A rib 20 is formed between the flange 19 and the outer peripheral portion 17.

The main-body second member 22 includes a main-body flow-path portion 23 that serves as the flow path of the air, a ring-shaped bottom portion 24 that is formed on the outer periphery of the main-body flow-path portion 23, and a cylindrical inner circumferential portion 25 that projects upward from the circumferential edge of the bottom portion 24. The main-body flow-path portion 23 is located at the center of the bottom portion 24. An upper portion of the main-body flow-path portion 23 projects upward from the bottom portion 24, and a lower portion of the main-body flow-path portion 23 projects downward from the bottom portion 24. An air guiding portion 27 that serves as a fluid guiding portion is formed at an upper end portion of the main-body flow-path portion 23. The air guiding portion 27 is formed by forming the upper end portion of the main-body flow-path portion 23 such that the thickness of the upper end portion decreases toward the upper side, and the air guiding portion 27 is an inclined surface that is inclined outward and upward. An accommodation gap 26 that is a portion of the accommodation space 21 is formed between the main-body flow-path portion 23 and the inner circumferential portion 25.

The movable nozzle portion 30 includes a cylindrical nozzle flow-path portion 31 that serves as the flow path of the air and a ring-shaped support-plate portion 37 that is formed on the outer periphery of the nozzle flow-path portion 31. The nozzle flow-path portion 31 includes a nozzle downstream flow-path portion 32 and a nozzle intermediate flow-path portion 34 that are respectively located on the upper side and the lower side while the support-plate portion 37 functions as the boundary therebetween. The ejection port 33 is formed in a side surface of the nozzle downstream flow-path portion 32 in such a manner as to be in the vicinity of the upper end of the nozzle downstream flow-path portion 32. The inner side of the nozzle intermediate flow-path portion 34 serves as a surrounding-wall portion 35, and the diameter of the nozzle intermediate flow-path portion 34 is larger than the diameter of the nozzle downstream flow-path portion 32. An air receiving portion 36 that serves as a fluid receiving portion is formed at a position corresponding to the lower end of the nozzle downstream flow-path portion 32 and the upper end of the nozzle intermediate flow-path portion 34. The air receiving portion 36 is formed in a ring-like shape around the nozzle downstream flow-path portion 32 and is an inclined surface that is inclined outward from the nozzle downstream flow-path portion 32 and inclined upward. A plurality of guide projections 38 is formed on the circumferential edge of the support-plate portion 37. The guide projections 38 are arranged in such a manner as to be equally spaced in the circumferential direction of the support-plate portion 37. Nozzle grooves 39 are formed in the respective upper surfaces of the guide projections 38.

The movable nozzle portion 30 is attached to the main-body second member 22 of the main body 10, and the O-ring 3 is attached to the movable nozzle portion 30. The coil spring 2 is interposed between the movable nozzle portion 30 and the main-body first member 11 of the main body 10, and the main-body first member 11 is assembled to the main-body second member 22. More specifically, the nozzle intermediate flow-path portion 34 of the movable nozzle portion 10 is inserted between the main-body flow-path portion 23 of the main-body second member 22 and the inner circumferential portion 25 and disposed in the accommodation gap 26 of the main-body second member 22. In this case, the surrounding-wall portion 35 of the nozzle intermediate flow-path portion 34 extends downward from the air receiving portion 36 and covers the exterior of the upper portion of the main-body flow-path portion 23.

The O-ring 3 is placed onto the support-plate portion 37 by passing through the nozzle downstream flow-path portion 32 of the movable nozzle portion 30. The lower end of the coil spring 2 is secured to the nozzle grooves 39 of the movable nozzle portion 30. The main-body first member 11 is assembled to the main-body second member 22 in the state in which the movable nozzle portion 30, the coil spring 2, and the O-ring 3 are accommodated in the accommodation space 21, and the outer peripheral portion 17 of the main-body first member 11 is fitted onto the exterior of the inner circumferential portion 25 of the main-body second member 22.

In the accommodation space 21, the guide projections 38 of the movable nozzle portion 30 are fitted into the respective guide grooves 18 of the outer peripheral portion 17. The nozzle flow-path portion 31 of the movable nozzle portion 30 communicates with the main-body flow-path portion 23, which projects toward the accommodation space 21, and the nozzle downstream flow-path portion 32 is inserted in the hole 13 of the exposed-surface portion 12 so as to be capable of extending through the hole 13. In other words, the main-body flow-path portion 23, the nozzle flow-path portion 31, and the hole 13 are arranged coaxially with each other so as to form a linear flow path. The air receiving portion 36 of the movable nozzle portion 30 is positioned so as to face the air guiding portion 27, which corresponds to the upper end of the main-body flow-path portion 23, and a gap is formed between the air receiving portion 36 and the air guiding portion 27.

The upper end of the coil spring 2 is secured to the main-body groove 16 of the main-body first member 11. In other words, the coil spring 2 is sandwiched between the exposed-surface portion 12 and the support-plate portion 37 and pushes the support-plate portion 37 while being compressed.

As illustrated in FIG. 4(a), the movable nozzle portion 30 is disposed at the non-usage position as a result of the support-plate portion 37 being pushed by the restoring force of the coil spring 2. At the non-usage position, the nozzle flow-path portion 31 is accommodated in the accommodation space 21, and the upper end of the nozzle flow-path portion 31 is aligned with an upper surface of the exposed-surface portion 12. The ejection port 33 is closed as a result of facing the sealing projection 14 and blocked by the main body 10. In this state, when a pump (not illustrated) operates, and the air is supplied to the main-body flow-path portion 23 from below, the movable nozzle portion 30 moves upward.

In other words, when the air flows through the main-body flow-path portion 23, the flow path of the air is changed by the Coanda effect in the air guiding portion 27, and the air flows along the air guiding portion 27. The air flows into the gap between the air receiving portion 36 and the air guiding portion 27 and is guided to the air receiving portion 36 of the movable nozzle portion 30. The air is pressurized in the air receiving portion 36, and the movable nozzle portion 30 is pushed by this pressure and moves upward against the restoring force of the coil spring 2. When the air is pressurized in the accommodation space 21, since the ejection port 33 is closed as a result of facing the sealing projection 14, and the upper portion of the main-body flow-path portion 23 is surrounded by the surrounding-wall portion 35 of the nozzle intermediate flow-path portion 34, leakage of the air does not occur.

As a result of moving, the movable nozzle portion 30 is disposed at the usage position as illustrated in FIG. 4(b). At the usage position, the coil spring 2 is compressed between the exposed-surface portion 12 and the support-plate portion 37, and the O-ring 3 is sandwiched between the step portion 15 and the support-plate portion 37. At the same time, the upper end of the nozzle downstream flow-path portion 32 projects from the exposed-surface portion 12, and the ejection port 33 is displaced from the sealing projection 14 and exposed to the outside. The air is ejected from the ejection port 33. In other words, the air pushes out the movable nozzle portion 30 and is ejected from the exposed ejection port 33. When the air is ejected, the space between the exposed-surface portion 12 and the support-plate portion 37 is sealed with the O-ring 3, and since the upper portion of the main-body flow-path portion 23 is surrounded by the surrounding-wall portion 35 of the nozzle intermediate flow-path portion 34, the air does not leak from any portion other than the ejection port 33.

When supply of the air is stopped, the support-plate portion 37 is pushed by the restoring force of the coil spring 2, so that the movable nozzle portion 30 moves downward and returns to the non-usage position.

The nozzle device 1 is configured as describe above. Advantageous effects of the nozzle device 1 will now be described.

As described above, in the nozzle device 1, the air receiving portion 36 is formed at the position corresponding to the lower end of the nozzle downstream flow-path portion 32 and the upper end of the nozzle intermediate flow-path portion 34 (see FIGS. 1(a) and 1(b)). The air receiving portion 36 is formed in a ring-like shape around the nozzle downstream flow-path portion 32 and is an inclined surface that is inclined outward from the nozzle downstream flow-path portion 32 and inclined upward (see FIGS. 4(a) and 4(b)). In other words, the air receiving portion 36 is recessed toward a downstream side, and thus, the air flows into the air receiving portion 36 and is pressurized. The movable nozzle portion 30 is pushed by the air pressure in the air receiving portion 36 and moved to the usage position against the restoring force of the coil spring 2. Therefore, the air-use efficiency can be improved. This is independent of the specifications of the pump and thus does not affect the size, the weight, and the price of the pump.

In the nozzle device 1, the air guiding portion 27 is formed at the upper end portion of the main-body flow-path portion 23 (see FIGS. 1(a) and 1(b)). The air guiding portion 27 is formed by forming the upper end portion of the main-body flow-path portion 23 such that the thickness of the upper end portion decreases toward the upper side, and the air guiding portion 27 is an inclined surface that is inclined outward and upward (see FIGS. 4(a) and 4(b)). In other words, when the air flows through the main-body flow-path portion 23, the flow path of the air is changed by the Coanda effect in the air guiding portion 27, and the air flows along the air guiding portion 27. The air flows into the gap between the air receiving portion 36 and the air guiding portion 27 and is guided to the air receiving portion 36 of the movable nozzle portion 30. Therefore, the pressure in the air receiving portion 36 can be increased, and the movable nozzle portion 30 can be suitably pushed.

In other words, since the gap is formed between the air receiving portion 36 and the air guiding portion 27, the air flows into the gap and is guided to the air receiving portion 36 of the movable nozzle portion 30. Thus, the movable nozzle portion 30 can be suitably pushed by increasing the pressure in the air receiving portion 36, and the air-use efficiency can be improved.

In the nozzle device 1, the nozzle intermediate flow-path portion 34 of the movable nozzle portion 10 is inserted between the main-body flow-path portion 23 and the inner circumferential portion 25 of the main-body second member 22 and disposed in the accommodation gap 26 of the main-body second member 22 (see FIGS. 4(a) and 4(b)). The surrounding-wall portion 35 of the nozzle intermediate flow-path portion 34 extends downward from the air receiving portion 36 and covers the exterior of the upper portion of the main-body flow-path portion 23. In other words, the outer periphery of the main-body flow-path portion 23 is covered with the surrounding-wall portion 35, so that leakage of the air from a downstream end portion of the main-body flow-path portion 23 can be suppressed.

In the nozzle device 1, the ring-shaped sealing projection 14 is formed on the lower surface of the exposed-surface portion 12 in such a manner as to project around the periphery of the hole 13 (see FIGS. 1(a) and 1(b)). At the non-usage position, the nozzle flow-path portion 31 is accommodated in the accommodation space 21, and the ejection port 33 is closed as a result of facing the sealing projection 14 and blocked by the main body 10 (see FIGS. 4(a) and 4(b)). With this configuration, the air is supplied while the ejection port 33 is blocked, and thus, the air does not leak from the ejection port 33 and is pressurized in the flow path. Therefore, the air-use efficiency can be improved.

The nozzle device 1 ejects scented air. In other words, scented air is jetted out from the instrument panel or the console, so that various stimuli can be given to a driver and a fellow passenger in accordance with the type of scent. Examples of the scent include a scent having an effect of helping a driver stay awake and a scent having a relaxation effect.

In the nozzle device 1, the O-ring 3 is placed onto the support-plate portion 37 by passing through the nozzle downstream flow-path portion 32 of the movable nozzle portion 30 (see FIGS. 4(a) and 4(b)). At the usage position, the O-ring 3 is sandwiched between the step portion 15 and the support-plate portion 37. Therefore, generation of noise by contact between the exposed-surface portion 12 and the support-plate portion 37 can be suppressed, and when the air is ejected, a gap between the exposed-surface portion 12 and the support-plate portion 37 can be sealed with the O-ring 3.

In the nozzle device 1, the upper end of the coil spring 2 is secured to the main-body groove 16 of the main-body first member 11, and the lower end of the coil spring 2 is secured to the nozzle grooves 39 of the movable nozzle portion 30. In other words, the coil spring 2 is sandwiched between the exposed-surface portion 12 and the support-plate portion 37 and pushes the support-plate portion 37 while being compressed. With this configuration, when supply of the air is stopped, the support-plate portion 37 is pushed by the restoring force of the coil spring 2, so that the movable nozzle portion 30 can move downward and can return to the non-usage position.

Figure 5A:
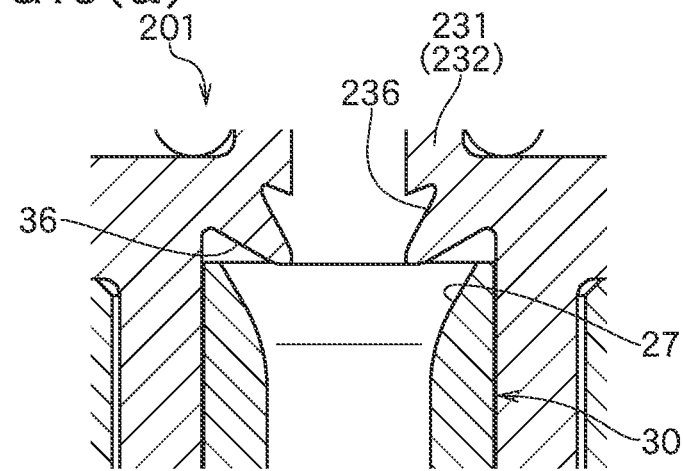
FIGS. 5(a), 5(b), and 5(c) illustrate principal portions of nozzle devices according to other embodiments of the present invention in an enlarged manner.
Figure 5B:
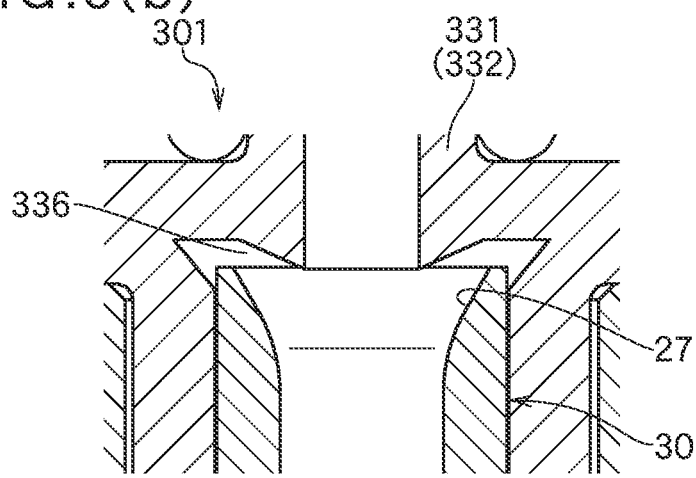
Figure 5C:
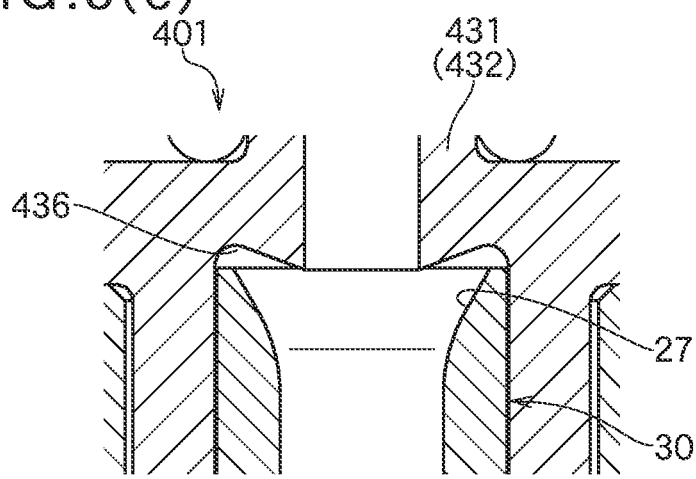

Nozzle devices according to the other embodiments of the present invention will now be described with reference to the drawings. FIGS. 5(a), 5(b), and 5(c) illustrate cross sections of principal portions of nozzle devices 201, 301, and 401 according to second to fourth embodiments of the present invention in an enlarged manner. Note that components that are different from those in the first embodiment will be mainly described below, and descriptions of components similar to those in the first embodiment will be suitably omitted.

As illustrated in FIG. 5(a), in the nozzle device 201 according to the second embodiment, an air receiving portion 236 is formed at an arbitrary position in a nozzle downstream flow-path portion 232. The air receiving portion 236 is formed in a ring-like shape around a nozzle flow-path portion 231 and is an inclined surface that is inclined outward and upward. With this configuration, the air flows into the air receiving portion 36 and the air receiving portion 236, and the movable nozzle portion 30 is pushed by the air pressure in the air receiving portion 36 and the air pressure in the air receiving portion 236 and moved to the usage position. Therefore, the air-use efficiency can be improved. Note that, although the air receiving portion 36 is provided in the present embodiment, as a modification of the present embodiment, a configuration may be employed in which the air receiving portion 36 is not provided and in which only a plurality of air receiving portions 236 is provided.

As illustrated in FIG. 5(b), in the nozzle device 301 according to the third embodiment, an air receiving portion 336 is formed of an inclined surface that is inclined outward from a nozzle downstream flow-path portion 332 and inclined upward and a flat surface that extends laterally from this inclined surface. Even with this configuration, advantageous effects the same as those of the first embodiment can be obtained.

As illustrated in FIG. 5(c), in the nozzle device 401 according to the fourth embodiment, an air receiving portion 436 is an inclined surface that is inclined outward from a nozzle downstream flow-path portion 432 and inclined upward, and the end of a recess is slightly rounded. Even with this configuration, advantageous effects the same as those of the first embodiment can be obtained.

Note that, as a first modification of each of the above-described embodiments, the air guiding portion 27 does not need to be provided as long as a gap is formed between the air receiving portion 36, 236, 336, or 436 and the upper end of the main-body flow-path portion 23. As a second modification, a configuration may be employed in which the ejection port is formed at upper end of the movable nozzle portion and in which a cover member is provided so as to open and close the hole of the main body. In this case, at the non-usage position, the cover member is closed, and when the movable nozzle portion moves to the usage position, the nozzle downstream flow-path portion pushes and opens the cover member, so that the ejection port is exposed. As a third modification, at the usage position, the ejection port may be exposed in the state in which the upper end of the movable nozzle portion is retracted downward from the exposed-surface portion. In other words, the usage position according to the present invention refers to a state where the air can be ejected from the ejection port and does not refer to the degree of projection of the movable nozzle portion with respect to the main body. As a fourth modification, the nozzle intermediate flow-path portion may be formed of a plurality of rod members that extends downward from the support-plate portion, and these rod members may be arranged in the circumferential direction of the air receiving portion with the nozzle downstream flow-path portion acting as the center. In other words, the surrounding-wall portion is not limited to being configured to entirely cover the exterior of the upper end portion of the main-body flow-path portion as in the first embodiment and may be partially discontiguous in the circumferential direction.

Although the embodiments of the present invention have been described in detail above, the present invention is not limited to the above-described embodiments. Various design changes can be made to the present invention as long as they are within the scope of the claims.

REFERENCE SIGNS LIST 1, 201, 301, 401 nozzle device
2 coil spring (first elastic member)
3 O-ring (second elastic member)
10 main body
11 main-body first member
12 exposed-surface portion
13 hole
14 sealing projection
15 step portion
16 main-body groove
17 outer peripheral portion
18 guide groove
19 flange
20 rib
21 accommodation space
22 main-body second member
23 main-body flow-path portion
24 bottom portion
25 inner circumferential portion
26 accommodation gap
27 air guiding portion (fluid guiding portion)
30 movable nozzle portion
31, 231, 331, 431 nozzle flow-path portion
32, 232, 332, 432 nozzle downstream flow-path portion
33 ejection port
34 nozzle intermediate flow-path portion
35 surrounding-wall portion
36, 236, 336, 436 air receiving portion (fluid receiving portion)
37 support-plate portion
38 guide projection
39 nozzle groove

The invention claimed is:

1. A nozzle device comprising:
a main body that is mounted on a vehicle body and that includes a main-body flow-path portion serving as a flow path of a fluid; and
a movable nozzle portion that is accommodated in the main body and that is caused, by a fluid, to move from a non-usage position at which an ejection port is accommodated in the main body to a usage position at which the ejection port is exposed outside of the main body,
wherein a nozzle flow-path portion is included in the movable nozzle portion and communicates with the main-body flow-path portion,
the nozzle flow-path portion includes a fluid receiving portion that is formed in such a manner as to extend upward and outward from an inner surface of the nozzle flow-path portion and in such a manner as to be inclined in a direction in which the movable nozzle portion moves to a usage position, and
wherein the movable nozzle portion includes a surrounding-wall portion that extends from the fluid receiving portion toward an upstream side of the flow path and that covers an outer periphery of the main-body flow-path portion.

2. The nozzle device according to claim 1,
wherein the fluid receiving portion is included in the nozzle flow-path portion and formed at a position facing a downstream end portion of the main-body flow-path portion, and
wherein a gap is formed between the fluid receiving portion and the downstream end portion.

3. The nozzle device according to claim 1,
wherein a downstream end portion of the main-body flow-path portion includes a fluid guiding portion having a broader flow-path than the upstream side and that is inclined in a direction in which the movable nozzle portion moves to a usage position.

4. The nozzle device according to claim 1, wherein the ejection port that is accommodated is blocked by the main body.

5. The nozzle device according to claim 1, wherein a fluid has a scent.

6. The nozzle device according to claim 1, wherein the main body includes
an accommodation space in which the movable nozzle portion is accommodated,
the main-body flow-path portion that has a downstream-side portion projecting toward the accommodation space, and
an exposed-surface portion that has a hole formed so as to be coaxial with the main-body flow-path portion and that is exposed to a side of a vehicle body on which a fluid is ejected,
wherein the movable nozzle portion includes a support-plate portion that is formed on an outer periphery of the nozzle flow-path portion,
wherein the ejection port is formed in a side surface of the nozzle flow-path portion, wherein, in the accommodation space, a first elastic member and a second elastic member are provided between the exposed-surface portion and the support-plate portion, the first elastic member being configured to move the movable nozzle portion, and the second elastic member being interposed between the exposed-surface portion and the support-plate portion.

7. The nozzle device according to claim 1,
wherein a fluid is air.

8. The nozzle device according to claim 1,
wherein the fluid receiving portion is recessed toward a downstream side of the flow path.

* * * * *